United States Patent [19]

Oki et al.

[11] Patent Number: 5,292,506
[45] Date of Patent: Mar. 8, 1994

[54] MURAMYLDIPEPTIDE DERIVATIVES AND INFLUENZA VACCINE COMPRISING THE DERIVATIVES

[75] Inventors: Masaharu Oki, Urayasu; Hideya Tsuge, Chiba; Kunio Ohkuma; Tetsuya Oka, both of Kumamoto, all of Japan

[73] Assignees: Daiichi Pharmaceutical Co., Ltd., Tokyo; The Chemo-Sero-Therapeutic Research Institute, Kumamoto, both of Japan

[21] Appl. No.: 783,148

[22] Filed: Oct. 28, 1991

[30] Foreign Application Priority Data

Oct. 30, 1990 [JP] Japan .................................. 2-293335
Oct. 30, 1990 [JP] Japan .................................. 2-293336

[51] Int. Cl.$^5$ .................... A61K 39/12; A61K 37/00; A61K 37/10; C07K 9/00
[52] U.S. Cl. .................................. 424/89; 424/88; 514/8
[58] Field of Search ................ 424/89, 88; 514/8

[56] References Cited

U.S. PATENT DOCUMENTS

4,895,835 1/1990 Hasegawa ............................ 514/8

FOREIGN PATENT DOCUMENTS

0135788 4/1985 European Pat. Off. .
0205098 6/1986 European Pat. Off. .
5010197/13 10/1991 U.S.S.R. .

OTHER PUBLICATIONS

Nagao et al., Infect. Immun. 55:1279-1288 (1987).

*Int. Congr. Sgr.-Excerpta Med.,* vol. 536, 1982, pp. 151-154.
*Infection and Immunity,* vol. 49, No. 1, Jul. 1985, pp. 244-249.
*Infection and Immunity,* vol. 53, No. 3, Sep. 1986, pp. 511-516.
*Infection and Immunity,* vol. 4, No. 1, Apr. 1983, pp. 16-21.
*Chemical Abstracts* 182620q.
Furuya et al., "Enhancement of Immunoglobulin G Responses in Mice Against Hepatitis B Virus Surface Antigen, Influenza Virus Hemagglutinin Vaccine, and Tetanus Toxoid by 6-O-Acylated Muramyl Dipeptides," *Infection and Immunity,* vol. 57, No. 6, Jun. 1989, pp. 1839-1844.
Nerome et al., "Development of a new type of influenza subunit vaccine made by muramyldipeptide-liposome: enhancement of humoral and cellular immune responses," *Vaccine,* vol. 8, Oct. 1990, pp. 503-509.

*Primary Examiner*—Christine M. Nucker
*Assistant Examiner*—M. P. Woodward
*Attorney, Agent, or Firm*—Burns, Doane, Swecker & Mathis

[57] ABSTRACT

Novel muramyldipeptide derivatives such as [6-0-(2-tetradecylhexadecanoyl)-N-acetylmuramoyl]-L-alanyl-D-glutamamide and [6-0-(2-tetradecylhexadecanoyl)-N-acetylmuramoyl]-L-alanyl-N -methyl-D-glutamamide are provided. The muramyldipeptide derivatives are excellent compound as an adjuvant or a constituting component of virosome vaccine. An influenza vaccine comprises a complex of the muramyldipeptide derivative and an influenza virus antigen. The influenza vaccine has excellent antibody-producing capacity and safety.

15 Claims, 2 Drawing Sheets

MURAMYLDIPEPTIDE DERIVATIVES AND INFLUENZA VACCINE COMPRISING THE DERIVATIVES

BACKGROUND OF THE INVENTION

The present invention relates to muramyldipeptide derivatives which have adjuvant activity and are useful as a component of influenza virus particle-like artificial membrane vaccine, so-called virosome vaccine. The present invention also relates to an influenza vaccine comprising a complex of the muramyldipeptide derivatives and an influenza virus antigen.

Since the effectiveness of presently used influenza HA vaccines varies due to mutations which occur on hemagglutinin molecule of the prevailing virus, it is eagerly desired to develop more effective vaccines than the conventional ones.

As for the recent approaches in influenza vaccine development, a component vaccine consisted of HA (hemagglutinin) and NA (neuraminidase) as main ingredients or influenza virus particle-like artificial membrane vaccine made from 6-0-(2-tetradecylhexadecanoyl)-N-acetylmuramoyl-L-alanyl-D-isoglutamine, so-called virosome vaccine, are known [see Japanese Patent Unexamined Published Application (hereinafter referred to as "J. P. KOKAI") No. 61-282321]. It is known that particularly the latter exhibits an excellent effect of improving antibody value in the blood and the utilization thereof is expected.

However, this vaccine irritates a part of a human body to which it is applied to cause a redness as an undesirable adverse reaction and it is not satisfactory as a medicine.

SUMMARY OF THE INVENTION

An object of the present invention is to provide novel muramyldipeptide derivatives which are practically useful as a component of virosome vaccine.

Another object of the present invention is to provide an influenza vaccine having excellent antibody-producing capacity and safety.

These and other objects of the present invention will be apparent from the following description and Examples.

After intensive investigations made for the purpose of solving the above-described problems, the inventors have completed the present invention.

According to the first aspect of the present invention, there is provided muramyldipeptide derivatives of the following general formula (I) and salts thereof:

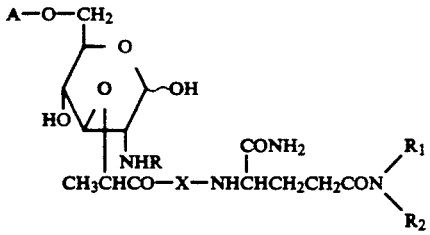

(I)

wherein R represents an acyl group having 2 to 6 carbon atoms, X represents L-alanine residue, L-serine residue, L-valine residue or glycine residue, A represents a fatty acid residue having 10 to 60 carbon atoms, and $R_1$ and $R_2$ independently represent a hydrogen atom, a substituted or unsubstituted lower alkyl group, a substituted or unsubstituted cycloalkyl group, a substituted or unsubstituted aryl group, a substituted or unsubstituted aralkyl group, a hydroxyl group, a lower alkoxy group, an amino group or a lower alkylamino group or $R_1$ and $R_2$ may form a cyclic amino group together with nitrogen atom to which $R_1$ and $R_2$ bond directly, which cyclic amino group may have one or more hetero atoms selected from the group consisting of oxygen, sulfur and nitrogen atoms as a ring-constituting atom and may be substituted or unsubstituted.

According to the second aspect of the present invention, there is provided an influenza vaccine comprising a complex of the compound of the general formula (I) mentioned above or a salt thereof and influenza virus antigen.

DESCRIPTION OF THE PREFERRED EMBODIMENTS

Figure 1:
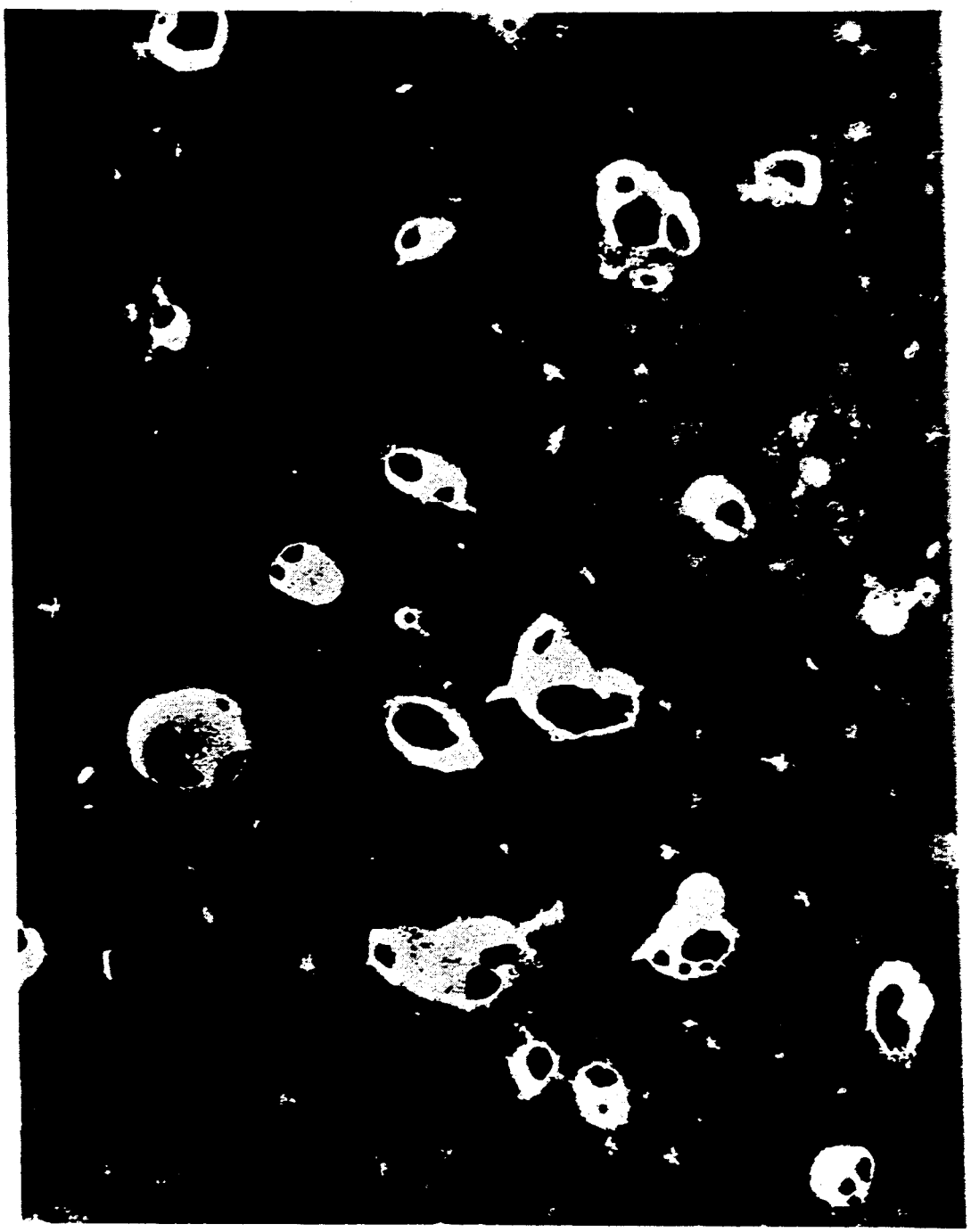
FIG. 1 is an electron photomicrograph (×95,000) of a vaccine of sample No. 1 of the present invention.

The description will be made on the substituents in the above formula (I).

The acyl groups having 2 to 6 carbon atoms include acetyl, propionyl, butyryl groups, etc. The fatty acid residues include straight chain or branched chain fatty acid residues having 20 to 60 carbon atoms which may have one or more unsaturated bonds. Examples of them include decanoyl, dodecanoyl, tridecanoyl, tetradecanoyl, hexadecanoyl, octadecanoyl, eicosanoyl, docosanoyl, tetracosanoyl, hexacosanoyl, triacontanoyl, tetracontanoyl, 9-hexadecenoyl, 9-octadecenoyl, 11,14-eicosadienoyl, 11-eicosenoyl, 11,14,17-eicosatrienoyl, 2-dodecylhexadecanoYl, 2-tetradecylhexadecanoyl, -2dodecyltetradecanoyl, 2-tetradecenylhexadecanoyl, 2-tetradecenylhexade canoyl, 2-hexadecyloctadecanoyl groups and the like. They are preferably branched chain ones having 20 to 40 carbon atoms.

The lower alkyl groups include those having 1 to 6 carbon atoms such as methyl, ethyl, propyl, isopropyl, tert-butyl groups and the like. The lower alkyl groups may have substituents such as halogen atoms, hydroxyl group, amino group and the like. The number of the substituents is usually preferably 1 to 3.

The cycloalkyl groups ar 5 to 7-membered ones such as cyclopropyl, cyclopentyl, cyclohexyl, cycloheptyl groups and the like. The cycloalkyl groups may have one or more substituents which include a lower alkyl group, a halogen atom, a hydroxyl group, an amino group and the like. The number of the substituents is usually preferably 1 to 3.

Examples of the halogen atom include chlorine, bromine, fluorine and iodine atoms.

The aryl groups include phenyl, naphthyl, biphenyl groups and the like. The aryl groups may have one or more substituents which include a lower alkyl group, a halogen atom, a hydroxyl group, an amino group and the like. The number of the substituents is usually preferably 1 to 3.

The aralkyl groups include, for example, phenylmethyl, phenylethyl, naphthylmethyl groups and the like. The aryl moiety of the aralkyl groups may have one or more substituents which include a lower alkyl group, a halogen atom, a hydroxyl group, an amino group and the like. The number of the substituents is usually preferably 1 to 3.

The cyclic amino groups include 5- to 7-membered cyclic amino groups such as pyrrolidinyl, piperidinyl, homopiperidinyl groups and the like. The cyclic amino groups may contain one or more hetero atoms, preferably one hetero group selected from the group consisting of oxygen, sulfur and nitrogen atoms as the ring-constitiuting atoms. Examples of them include 3-oxazolidinyl, 3-thiazolidinyl, morpholino, thiomorpholino, 1-pyrazolidinyl, 1-imidazolidinyl groups and the like. The cyclic amino groups may have one or more substituents which include a lower alkyl group, a halogen atom, a hydroxyl group, an amino group and the like. The number of the substituents is usually preferably 1 to 3. Examples of the lower alkoxy group include methoxy, ethoxy, propoxy, isopropoxy and the like. The alkylamino group means a mono-lower alkylamino group or a di-lower alkylamino group, and examples thereof include monomethylamino, monoethylamino, dimethylamino, dipropylamino, monobutylamino and the like.

A partial structure —NHCH(CONH$_2$)CH$_2$CH$_2$CO— of the compound of the formula (I) has D- and L-isomers, since it has an asymmetric carbon atom. Usually the D-isomer is preferred.

As for the 1-position of the saccharose part of the compound of the formula (I), it has anomeric isomers ($\alpha$- and $\beta$-isomers), both of which are usable for the vaccine regarding the present invention.

For convenience' sake, both anomeric isomers are herein represented at the same time by the following partial structural formula:

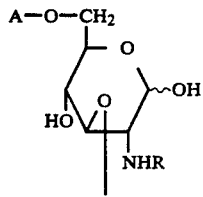

Description will be made on processes for producing the compounds of the formula (I):

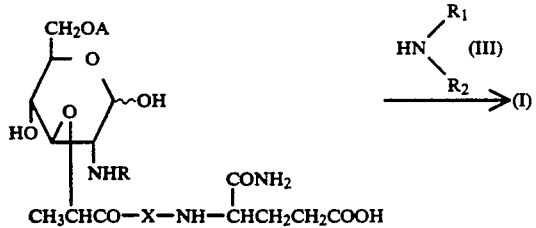

Namely, a compound of the formula (II) can be reacted with a compound of the formula (III) by a condensation method frequently employed in the synthesis of peptides such as carbodiimide method, eintopf method or active ester method to form an intended compound of the formula (I). For example, when the active ester method is employed usually, a compound of the formula (II) is dissolved in an inactive organic solvent such as dimethylformamide, tetrahydrofuran, dioxane, acetonitrile or a mixture thereof and reacted with a reagent to form the active ester such as N,N-disuccinimidyl carbonate, N,N-carbonylimidazole or N,N-disuccinimidyl oxalate, preferably, in the presence of an organic base such as triethylamine, N-methylmorpholine or 4-dimethylaminopyridine at 0° C. to about 60° C. for 30 min to several hours to form an active ester, to which an amine compound of the formula (III) is added in the presence of a base such as the above-described bases at a temperature of about −15° C. to about 60°, preferably 0° C. to 25° C. and the reaction can be conducted for several-ten minutes to about one day. The above reagent to form the active ester can be used in equimolar amount to the compound of the formula (II). The above organic base can be also used equimolar or excess to the compound of the formula (II). Then the resulting product is purified by silica gel column chromatography or the like to obtain the compound of the formula (I).

The starting compound of the formula (II) can be prepared according to the process described in Japanese Patent Publication No. 63-11359.

The complex constituting the vaccine of the present invention is such that a compound of the formula (I) or its salt aggrigates with, if desired, a lipid to form a closed endoplasmic reticulum and the influenza virus antigen is incorporated in the membrane thereof. Typical example therof is virus particle-like vaccine, i.e. so-called virosome.

The description will be made on the antigen in the vaccine of the present invention.

The antigens usable in the present invention include HA (hemagglutinin) antigen, NA (neuraminidase) antigen of influenza virus and the like. Usually a mixture of them, i.e. so-called HANA antigen, is desirably used. The HANA antigen can be obtained by purifying influenza virus by low-speed and high-speed centrifugal separation treatments or chemical treatment of allantoic fluid infected with influenza virus, solubilizing the purified virus with a surfactant such as Triton X-100, sodium cholate or the like, or separating the virus with an organic solvent such as an ether and purifying and isolating by sucrose density-gradient centrifugation, affinity chromatography or the like. The antigen thus obtained is used in an amount of usually 1/300 to 10 parts by weight, preferably 1/100 to 1 part by weight, per 1 part by weight of the compound of the formula (I) or its salt.

The vaccine of the present invention can be produced by various processes such as an ordinary process for producing liposome. Typical examples of the processes will be described below.

The influenza virus antigen, a compound of the formula (I) or its salt and preferably a phospholipid are mixed together in a suitable buffer solution such as a phosphate buffer solution or the like and an effective amount (preferably 0.1 to 20 w/v %) of a surfactant such as sodium cholate, octyl glycoside or the like is added to the mixture to solubilize it. The mixture is then dialyzed to remove the used surfactant, thereby obtaining the influenza vaccine of the present invention. A saccharide such as glucose, maltose or lactose, a salt such as sodium chloride, or a mixture thereof may be incorporated as an isotonizer into the vaccine of the present invention thus obtained.

Examples of the phospholipids include phosphatidyl glycerols such as dimyristoylphosphatidyl glycerol and dipalmitoylphosphatidyl glycerol; phosphatidyl serine; phosphatidyl cholines such as dipalmitoylphosphatidyl choline; phosphatidyl ethanolamine; phosphatidylinositol; phosphatidic acid and the like. They can be derived from a natural substance such as egg yolk or soy beans or they can be synthetic ones. They can be used either singly or in the form of a mixture. The amount of them used is usually 1/20 to 20 parts by weight, preferably ¼ to 3 parts by weight, per 1 part by weight of the compound of the formula (I) or its salt.

In the above-described process, the phospholipid can be used in combination with cholesterol, α-tocopherol, dicetyl phosphate, stearylamine or the like which is used in an amount of usually not more than 2 parts by weight, preferably 1/10 to ½ part by weight, per 1 part by weight of the compound of the formula (I) or its salt.

The vaccine of the present invention thus produced is usually in such a form that a compound of the formula (I) or its salt and the phospholipid form particles and the antigen is incorporated in the membrane thereof, which is so-called virosome. The average particle diameter of the virosome and zeta-potential of the surface can be controlled by varying the ratio of the compound of the formula (I) or its salt to the phospholipid. Usually the average particle diameter of the virosome is preferably 40 to 300 nm and zeta-potential thereof is preferably −5 to +70 mV.

The vaccine of the present invention is usually given by subcutaneous administration. 350 to 12 μg (in terms of antigen protein) of the vaccine is administered once to several times in a season.

Muramyldipeptide derivatives of the present invention have an excellent adjuvant activity and are excellent components of virosome vaccine.

The vaccine of the present invention has an antibody-producing capacity equivalent to or higher than that of conventional virosome vaccine and far higher safety in the viewpoints of redness and fever. In addition, the vaccine of the present invention has a high stability also during storage and it can be stored in frozen form or freeze-dried form.

The following Examples will further illustrate the present invention, which by no means limit the invention.

EXAMPLE 1

1.0 g of [6-0-(2-tetradecylhexadecanoyl)-N-acetylmuramoyl]-L-alanyl-D-isoglutamine was dissolved in 100 ml of tetrahydrofuran. 0.3 g of N,N-disuccinimidyl carbonate and 0.15 ml of triethylamine were added to the solution and they were stirred at room temperature for 1.5 hours. 0.22 ml of 28% aqueous ammonia was then added to them and they were stirred at room temperature for additional 30 minutes.

The reaction liquid was concentrated under reduced pressure and the residue was subjected to silica gel column chromatography. After purification by eluation with chloroform/methanol followed by freeze-drying from water/dioxane, 0.44 g of [6-0-(2-tetradecylhexadeca noyl)-N-acetylmuramoyl]-L-alanyl-D-glutamamide was obtained.

Melting point: 155° to 165° C.

Molecular weight: 926 ($C_{49}H_{91}N_5O_{11}$): FAB Mas m/z 927 (M+1)

$^1$H-NMR (DMSO-$d_6$) δ: 0.85 (6H, t, J=7Hz), 1.2 to 1.3, 1.39, 1.50 (58H,m), 1.72 (1H, m), 1.80 (3H, s), 1.93 (1H,m), 2.08 (2H, t, J=8Hz), 2.30 (1H, m), 3.28 (1H, t, J=9Hz), 3.46 (1H, t, J=9Hz), 3.67 (1H, m), 3.81 (1H, m), 4.02 (1H, d-d, J=12Hz, 5Hz}, 4.12 (1H, d-q, J=9Hz, 5Hz), 4.31 (2H, m), 4.34 (1H, d, J=10Hz), 4.44 and 4.98 (1H), 5.43 (1H, d, J=4Hz), 6.67 (1H, d, J=4), 6.74 (1H, s), 7.01 (1H, s), 7.27 (1H, s), 7.30 (1H, s), 7.65 (1H, d, J-7Hz), 8.08 (1H, d, J=8Hz), 8.17 (1H, d, J=8Hz).

EXAMPLE 2

1.0 g of [6-0-(2-tetradecylhexadecanoyl)-N-acetylmuramoyl]-L-alanyl-D-isoglutamine was dissolved in 100 ml of tetrahydrofuran. 0.3 g of N,N-disuccinimidyl carbonate and 0.15 ml of triethylamine were added to the solution. They were stirred at room temperature for 1.5 hous. 0.2 ml of 40% aqueous methylamine solution was added to them and they were stirred at room temperature for additional 30 minutes.

The reaction liquid was concentrated under reduced pressure and the residue was subjected to silica gel column chromatography. After purification by eluation with chloroform/methanol followed by freeze-drying from water/dioxane, 0.5 g of [6-0-(2-tetradecylhexadecan oyl)-N-acetylmuramoyl]-L-alanyl-N -methyl-D-glutamamide was obtained.

Melting point: 95° to 100° C.

Molecular weight: 939 ($C_{50}H_{93}N_5O_{11}$): FAB Mas m/z 940 (M+1)

$^1$H-NMR (DMSO-$d_6$) δ: 0.85 (6H, t, J=7Hz), 1.2 to 1.3, 1.39, 1.50 (58H, m), 1.73 (1H, m), 1.79 (3H, s), 1.93 (1H, m), 2.07 (2H, t, J=8Hz), 2.30 (1H, m), 2.55 (3H, d, J=5Hz), 3.26 (1H, t, J=9Hz), 3.46 (1H, t, J=9Hz), 3.68 (1H, m), 3.82 (1H, m), 4.03 (1H, d-d, J=12Hz, 5Hz), 4.12 (1H, d-q, J=9Hz, 5Hz), 4.30 (2H, m), 4.36 (1H, d, J=10Hz), 4.98 (1H, t, J=3.5 Hz), 5.43 (1H, d, J=7Hz), 6.67 (1H, d, J=4Hz), 7.01 (1H, s), 7.31 (1H, s), 7.64 (1H, d, J=7Hz), 7.71 (1H, d, J-5Hz), 8.07 (1H, d, J=8Hz), 8.17 (1H, d, J=8Hz).

EXAMPLE 3

[6--0-(2-Tetradecylhexadecanoyl)-N-acetylmuramoyl]-L-alanyl-N-ethyl-D-glutamamide was produced in the same manner as that of Example 2.

Molecular weight: 953 ($C_{51}H_{95}N_5O_{11}$): FAB Mas m/z 954 (M+1)

$^1$H-NMR (DMSO-$d_6$) δ: 0.85 (6H, t, J=7Hz), 0.99 (3H, t, J=7Hz), 1.2 to 1.3, 1.39, 1.50 (58H, m), 1.71 (1H, m), 1.79 (3H, s), 1.93 (1H, m), 2.06 (2H, t, J=8Hz), 2.29 (1H, m), 3.04 (2H, d-q, J=3, 5Hz, 7Hz), 3.28 (1H, t, J=9Hz), 3.45 (1H, t, J=9Hz), 3.68 (1H, m), 3.81 (1H, m), 4.03 (1H, d-d, J=12Hz, 5Hz), 4.12 (1H, d-q, J=9Hz, 5Hz), 4.29 (2H, m), 4.35 (1H, d, J=10Hz), 4.97 (1H, t, J=3.5 Hz), 5.44 (1H, d, J=7Hz), 6.68 (1H, d, J=4Hz), 7.01 (1H, s), 7.30 (1H, s), 7.64 (1H, d, J=7Hz), 7.76 (1H, d, J=5.5Hz), 8.07 (1H, d, J=8Hz), 8.16 (1H, d, J=8Hz).

EXAMPLE 4

Preparation of Influenza HANA Antigen

Purified virus was obtained from allantoic fluid infected with influenza A/Yamagata/120/86 strain by high-speed centrifugal treatment (23,000 rpm, 90 min), low-speed centrifugal treatment (6,000 rpm, 60 min) and sucrose density-gradient centrifugation (30,000 rpm, 3 h). Then Triton X-100 was added to the virus solution in such an amount that the concentration of Triton X-100 would be 1%. They were thoroughly stirred to solubilize the virus and then the pufified HANA antigen solution was obtained by sucrose density-gradient equilibrium method.

Preparation of Virosome Vaccine

Figure 2:
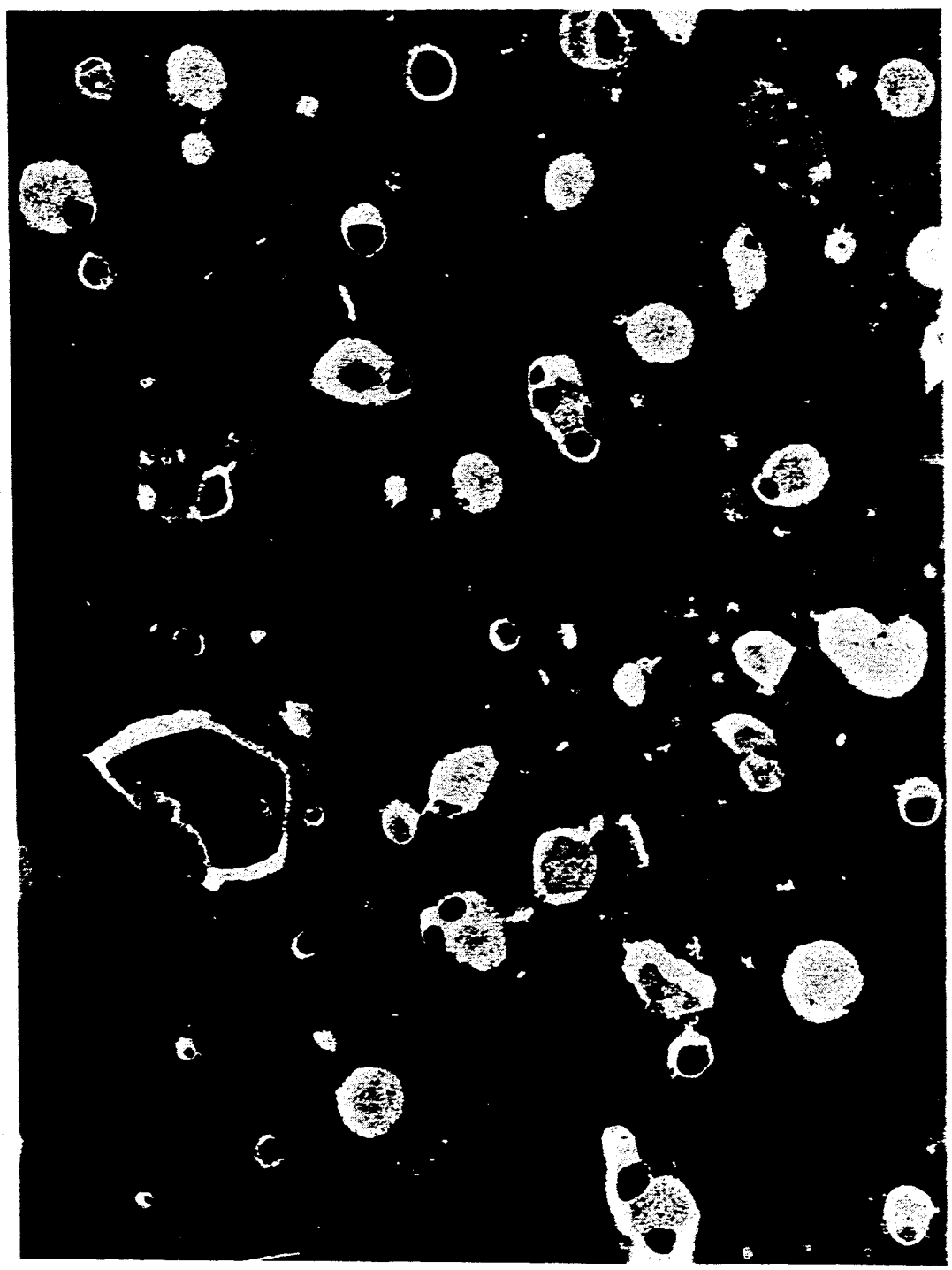
FIG. 2 is an electron photomicrograph (×95,000) of a vaccine of sample No. 2 of the present invention.

From the purified HANA antigen solution obtained above, four kinds of vaccine samples each having a composition shown in Table 1 were prepared as follows: the respective ingredients were mixed together and then octyl glucoside was added to the mixture in such an amount that the concentration thereof would be 4% to solubilize the ingredients. Then dialysis was conducted with 5% glucose-containing phosphate buffer solution (pH 7.4) according to the conventional method. The HANA antigen concentration of each sample thus obtained was adjusted to 70 μg/ml. Virosome formation was observed in the resulting sample virosome in the Sample Nos. 1 and 2 of the present invention are shown in FIGS. 1 and 2.

The virosome vaccine (No. 1 or 2) of the present invention and control vaccine were diluted to a concentration of 1/15 to the former vaccine solution and subcutaneously inoculated to the back of each of a group of 10 guinea pigs in an amount of 0.5 ml. Three weeks after the inoculation, it was inoculated again in the same amount. After 3 weeks and 5 weeks, blood was taken from the guinea pigs and subjected to Hemagglutinin Inhibition Test according to WHO method to determine antibody-forming capacity. The results are shown in Table 1.

TABLE 1

| Sample No. | Composition | | Antibody-forming capacity (HI value) | |
|---|---|---|---|---|
| | | | 3 week | 5 weeks |
| 1 | HANA | 70 μg | <80 | 5120 |
| | Compound of Ex. 1 | 300 μg | | |
| | Phosphatidyl choline | 225 μg | | |
| | Phosphatidyl glycerol | 150 μg | | |
| 2 | HANA | 70 μg | <80 | 2560 |
| | Compound of Ex. 2 | 300 μg | | |
| | Phosphatidyl choline | 225 μg | | |
| | Phosphatidyl glycerol | 150 μg | | |
| 3 | HANA | 70 μg | <80 | 2560 |
| | Compound of Ex. 1 | 600 μg | | |
| | Dimyristoylphosphatidyl choline | 450 μg | | |
| | Dimyristoylphosphatidyl glycerol | 300 μg | | |
| 4 | HANA | 70 μg | <80 | 2560 |
| | Compound of Ex. 1 | 600 μg | | |
| | Dimyristoylphosphatidyl glycerol | 600 μg | | |
| | Choresterol | 300 μg | | |
| Control 1 | HANA | 70 μg | <80 | 2560 |
| | Control compound* | 300 μg | | |
| | Choresterol | 300 μg | | |
| Control 2 | HANA | 70 μg | <80 | 1280 |
| Control 3 | HANA vaccine | 70 μg | <80 | 1280 |
| Control 4 | Formalin-inactivated whole particle vaccine | 70 μg | <80 | 1280 |

It is apparent from the above Table that the vaccines of the present invention exhibited an antibody-producing capacity equivalent to or higher than that of the control vaccines.

* Control compound: 6-0-(2-tetradecylhexadecanoyl)-N-acetylmuramoyl-L-alanyl-D-isoglutamine

Redness Reaction Test

In the redness reaction test, 0.5 ml of a sample was subcutaneously inoculated to the back of each of 5 rabbits, the red surface area of each rabbit was determined everyday, the total area of the five rabbits was calculated and then the average red surface area of the rabbits was calculated. The results are shown in Table 2.

TABLE 2

| | | Redness reaction test | | | |
|---|---|---|---|---|---|
| | | Positive animal | Red surface area (cm²) | | |
| Sample No. | Composition | (No.)/Tested animal (No.) | 1 day | 2 days | 3 days |
| 1 | HANA 70 μg | 1/5 | 1.1 | 0 | 0 |
| | Compound of Ex. 1  300 μg | | | | |
| | Phosphatidyl choline  225 μg | | | | |
| | Phosphatidyl glycerol  150 μg | | | | |
| 2 | HANA 70 μg | 1/5 | 1.0 | 0 | 0 |
| | Compound of Ex. 2  300 μg | | | | |
| | Phosphatidyl choline  225 μg | | | | |
| | Phosphatidyl glycerol  150 μg | | | | |
| Control 1 | HANA 70 μg | 5/5 | 5.7 | 4.2 | 8.5 |
| | Control compound  300 μg | | | | |
| | Cholesterol  300 μg | | | | |
| Control 2 | HANA vaccine | 3/5 | 4.5 | 4.0 | 1.6 |

It is apparent from the above table that degree of redness caused by the vaccines of the present invention was lower than that caused by the control vaccines.

Fever Test in the fever test, 1 ml of each sample was introduced into a vein of a rabbit according to Standard General Test of Biological Products. When the total of the fever elevated by the reaction of three rabbits was 1.3° C. or less, the results of the fever test were shown as negative and when it was 2.5° C. or more, the results were shown as positive. The results are shown in Table 3.

TABLE 3

| Sample No. | Composition | | Fever test (Total elevation of body temp. of 3 rabbits) |
|---|---|---|---|
| 1 | HANA | 70 μg | 0.81° C. |
| | Compound of Ex. 1 | 300 μg | Results: negative |
| | Phosphatidyl choline | 225 μg | |
| | Phosphatidyl glycerol | 150 μg | |
| 2 | HANA | 70 μg | 0.14° C. |
| | Compound of Ex. 2 | 300 μg | Results: negative |
| | Phosphatidyl choline | 225 μg | |
| | Phosphatidyl glycerol | 150 μg | |
| Control 1 | HANA | 70 μg | 2.66° C. |
| | Control compound | 300 μg | Results: positive |
| | Choresterol | 300 μg | |

It is apparent from the above Table that degree of elevation of fever caused by vaccines of the present invention was lower than that caused by the control vaccine.

What is claimed is

1. Muramyldipeptide derivatives of the following general formula (I) and salts thereof:

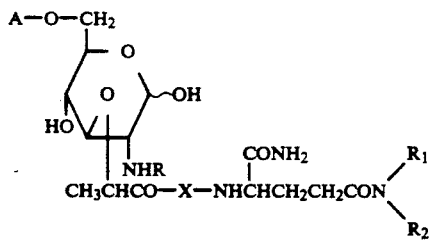

(I)

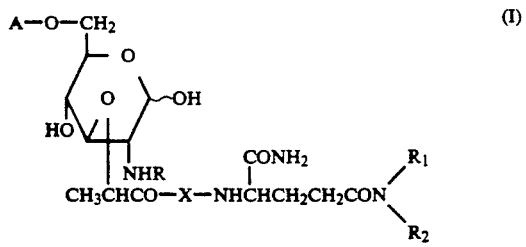

(I)

wherein R represents an acyl group having 2 to 6 carbon atoms, X represents L-alanine residue, A represents a branched fatty acid residue having 20 to 60 carbon atoms, and $R_1$ and $R_2$ independently represent a hydrogen atom or a substituted or unsubstituted lower alkyl group.

2. Muramyldipeptide derivatives of claim 1 wherein A represents a branched fatty acid residue having 20 to 40 carbon atoms.

3. Muramyldipeptide derivatives of claim 1 wherein the lower alkyl group has 1 to 6 carbon atoms.

4. Muramyldipeptide derivatives of claim 1 wherein R represents an acyl group having 2 to 6 carbon atoms, X represents L-alanine residue, A represents a branched chain fatty acid residue having 20 to 40 carbon atoms and $R_1$ and $R_2$ independently represent a hydrogen atom or a lower alkyl group.

5. A muramyldipeptide derivative selected from the group consisting of [6-0-(2-tetradecylhexadecanoyl)-N-acetylmuramoyl]-L-alanyl-D-glutamamide, [6-0-(2-tetradecylhexadecanoyl)-N-acetylmuramoyl]-L-alanyl-N-methyl-D-glutamamide and [6-0-(2-Tetradecylhexadecanoyl)-N-acetylmuramoyl]-L-alanyl-N-ethyl-D-glutamamide.

6. An influenza vaccine comprising a complex of a compound of the general formula (I):

wherein R represents an acyl group have 2 to 6 carbon atoms, X represent L-alanine residue, A represents a branched fatty acid residue having 20 to 60 carbon atoms, and $R_1$ and $R_2$ independently represent a hydrogen atom or a substituted or unsubstituted lower alkyl group or a salt thereof and influenza hemagglutinin neuraminidase antigen.

7. An influenza vaccine of claim 6 wherein A represent a branched fatty acid residue having 20 to 40 carbon atoms.

8. An influenza vaccine of claim 6 wherein R represents an acyl group having 2 to 6 carbon atoms, X represents L-alanine residue, A represents branched chain fatty acid residues having 20 to 40 carbon atoms and $R_1$ and $R_2$ independently represent a hydrogen atom or a lower alkyl group.

9. An influenza vaccine of claim 6 wherein the antigen is used in an amount of 1/300 to 10 parts by weight per 1 part by weight of the compound of the formula (I) or its salt.

10. An influenza vaccine of claim 6 wherein the compound of the formula (I) or its salt and a lipid form liposomes and the influenza hemagglutinin neuraminidose antigen is incorporated in the membrane thereof.

11. An influenza vaccine of claim 10 wherein the vaccine is a virosome vaccine having a diameter of 40 to 300 nm.

12. An influenza vaccine of claim 10 wherein R represents an acyl group having 2 to 6 carbon atoms, X represents L-alanine residue, A represents a branched fatty acid residue having 20 to 40 carbon atoms and $R_1$ and $R_2$ independently represent a hydrogen atom or a lower alkyl group.

13. An influenza vaccine of claim 10 wherein the lipid is a phospholipid and is used in an amount of 1/20 to 20 parts by weight per 1 part by weight of the compound of the formula (I) or its salt.

14. An influenza vaccine of claim 13 wherein the lipid is used in an amount of ¼ to 3 parts by weight per 1 part by weight of the compound of the formula (I) or its salt.

15. An influenza vaccine of claim 6 wherein the complex further comprises a phospholipid.

* * * * *